United States Patent [19]

Sieber et al.

[11] 4,358,439
[45] Nov. 9, 1982

[54] CYCLOOCTAPEPTIDES

[75] Inventors: Peter Sieber, Reinach; Bruno Kamber, Arlesheim; Hans Rink, Riehen, all of Switzerland

[73] Assignee: Ciba-Geigy Corporation, Ardsley, N.Y.

[21] Appl. No.: 216,353

[22] Filed: Dec. 15, 1980

[30] Foreign Application Priority Data

Dec. 21, 1979 [CH] Switzerland .............. 11409/79

[51] Int. Cl.³ .................. A61K 37/00; C07C 103/52
[52] U.S. Cl. ............................ 424/177; 260/112.5 S
[58] Field of Search ................ 260/112.5 S; 424/177

[56] References Cited

U.S. PATENT DOCUMENTS 3,725,380 4/1973 Konig et al. .
3,862,113 1/1975 Riniker et al. .
3,872,074 3/1975 Konig et al. .
3,875,207 4/1975 Iselin et al. .
3,944,590 3/1976 Iselin et al. .
4,146,612 3/1979 Veber ........................ 260/112.5 S
4,238,481 12/1980 Rink et al. .

OTHER PUBLICATIONS

Science 179, 77 (1973).

*Primary Examiner*—Delbert R. Phillips
*Attorney, Agent, or Firm*—Michael W. Glynn; Prabodh I. Almaula

[57] ABSTRACT

Cyclic peptides of the formula

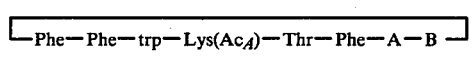

(I)

in which trp represents L-Trp, D-Trp, or an analogous radical which carries a halogen atom in the indole nucleus, $Ac_A$ represents hydrogen, or an acyl radical Ac of a carboxylic acid present at the ε-amino group, A represents L-Phe, D-Phe, L-Phg or D-Phg, or a corresponding radical having a substituted or saturated phenyl ring, and B represents the residue of a γ- or δ-amino-lower alkanecarboxylic acid which may carry an optionally substituted cyclic hydrocarbyl radical Ar, and also pharmacologically tolerable salts and therapeutically acceptable complexes thereof can be used as an antidiabetic in an analogous manner to somatostatin. They can be obtained by conventional processes of peptide chemistry, especially by cyclisation of corresponding linear peptides.

7 Claims, No Drawings

CYCLOOCTAPEPTIDES

The invention relates to novel cyclopeptides of the somatostatin type and processes for the manufacture thereof, and also pharmaceutical preparations containing these compounds and the use of these compounds and preparations for therapeutic purposes.

The invention relates especially to cyclopeptides that contain the most important features of somatostatin, such as the partial sequence of the amino acids 6–11 or an equivalent sequence, but, at the time, are free of sulphur. The somatostatin-analogous cyclopeptides according to the invention comprise cyclic octapeptides of the formula

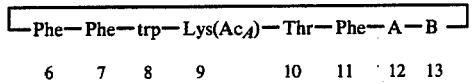

(I)

in which trp represents L-Trp, D-Trp or an analogous radical which carries in the indole nucleus a halogen atom, $Ac_A$ represents an acyl radical Ac of a carboxylic acid, present at the ε-amino group, or preferably represents hydrogen, A represents L-Phe, D-Phe, L-Phg or D-Phg (wherein Phg denotes a C-phenylglycyl radical), or a corresponding radical having a substituted or saturated phenyl ring, and B represents the residue of a γ- or δ-amino-lower alkanecarboxylic acid which may carry an optionally substituted cyclic hydrocarbyl radical Ar at one of its carbon atoms, and also salts and complexes thereof.

As is known, somatostatin, a cyclic tetradecapeptide of the formula

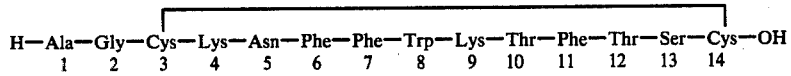

[Science 179, 77 (1973)], inhibits the pituitary-controlled secretion of the somatotrophic hormone (somatotrophin). It also inhibits the secretory activity of the endocrine pancreas, such as the secretion of insulin and glucagon. In the case of somatostatin itself, these valuable properties cannot be used fully in practice since this compound has too short a duration of action. In addition, it is often preferable for the active substance to exercise its inhibitory effect predominantly on one of the two glands, whilst the other gland should be affected as little as possible. (In most cases, the inhibition of the pituitary secretion, i.e. that of the somatotrophic hormone release, is less desirable.) For this reason, attempts are being made to achieve a dissociation of the inhibitory effects and a duration of action which is as long as possible by modifying the basic sequence, especially by omitting individual original amino acids and/or exchanging them for other, often "unnatural", amino acids. It has been found, for example, that especially advantageous physiological properties of this type occur in cyclopeptides of the type

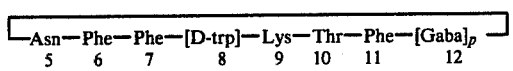

(M)

in which Gaba represents the residue of γ-aminobutyric acid and p represents the number 0, 1 or 2, and in other closely related compounds, cf. our European Patent Application No. 78 100 994.9, published under No. 0 001 295. A typical feature of these compounds is the presence of a straight carbon chain which is intended to simulate the original grouping —$CH_2$—S—S—$CH_2$— in the cystine residue of somatostatin.

Surprisingly, it has now been found that, by a very unusual modification of this simple, in each case unsubstituted, chain section, which comprises substitution with a cyclic hydrocarbyl radical, the desired activity is not only maintained but also further increased. For example, in the determination of the release of insulin and glucagon in the isolated, perfused rat pancreas stimulated with arginine [Method according to B. Petrack, A. J. Czernik, W. Itterly, J. Ansell and H. Chertock: Biochem. and Biophys. Res. Commun. 73, 934–939 (1976)], it has been found that [D-Trp$^8$, Phe$^{12}$, Gaba$^{13}$-]cyclosomatostatin(6–13)octapeptide exercises one to two times the inhibitory effect on insulin and glucagon secretion as compared with somatostatin.

In the compounds of the formula I defined at the beginning trp represents preferably D-Trp or alternatively an L- or D-Trp radical that carries in the indole nucleus, especially in the 5-position, a halogen atom, such as chlorine and especially fluorine, for example especially [D-(5F)Trp] which is derived from D-5-fluorotryptophan.

In the compounds of the formula I defined at the beginning, among the meanings of A there should be emphasized especially the radical L-Phe, and also D-Phe. A radical that corresponds to Phe or Phg and is saturated in the phenyl ring is a β-cyclohexylalanyl (Cha) or C-cyclohexylglycyl radical respectively; these may be in the L- or D-configuration. A radical that corresponds to the radical Phe or Phg and is substituted in the phenyl ring is one carrying one or two identical or different substituents of an aromatic ring from among those mentioned hereinbelow, for example L- or D-Tyr.

A γ-amino-lower alkanecarboxylic acid or a δ-amino-lower alkanecarboxylic acid mentioned under the symbol B in the formula I is one having from 4 to 8, especially 4 or 5, carbon atoms, preferably one having a straight carbon chain, especially δ-aminovaleric acid and more especially γ-aminobutyric acid (Gaba). If such an acid carries a hydrocarbyl radical Ar, the latter is located preferably in the β-position. An especially preferred radical of this kind is that of β-Ar-γ-aminobutyric acid [Gaba(Ar)]. Most preferred, however, are radicals of the said amino-lower alkanecarboxylic acids that are unsubstituted, such as especially Gaba.

The cyclic hydrocarbyl radical Ar is especially a mono- or bicyclic cycloalkyl radical or a corresponding aryl radical containing at least one aromatic ring and having a maximum of 12 ring carbon atoms. Of the cycloalkyl radicals, those that are preferred have 3- to 8-membered, and especially 5- and/or 6-membered, rings, such as, for example, cyclopropyl, cyclobutyl, cycloheptyl, cyclooctyl and more especially cyclopentyl and cyclohexyl. An aryl radical is a naphthyl radical, such as 1- or 2-naphthyl, a corresponding partially hydrogenated naphthyl radical, such as, especially, 1-, 2-, 5- or 6-(1,2,3,4-tetrahydronaphthyl), or a phenyl radical. These cyclic hydrocarbyl radicals may carry one or more alkyl radicals having a maximum of 4 carbon atoms, for example methyl, ethyl, propyl, isopropyl or butyl, and/or further cyclic, especially monocyclic, hydrocarbyl radicals, such as those defined above, the total number of carbon atoms being a maximum of 18. Examples of such cyclic hydrocarbyl radicals are 4,4-dimethylcyclohexyl, tolyl, such as 2-, 3- or 4-tolyl, and biphenylyl, for example 4-biphenylyl.

The aromatic moiety of the cyclic hydrocarbyl radicals may be substituted by one, two or more identical or different substituents, such as halogen, for example chlorine, bromine, iodine and especially fluorine, lower alkoxy, especially one derived from one of the above-mentioned lower alkyl radicals having a maximum of 4 carbon atoms, including, especially, methoxy, also nitro and amino, especially primary amino, di-lower alkylamino and acylamino, such as lower alkanoylamino, for example acetamino. Especially preferred are phenyl radicals substituted by the mentioned substituents. (In the same manner, the phenyl rings of Phe and Phg, as mentioned under the meanings of A, may also carry one or two identical or different substituents from among those mentioned, especially one in the 4-position.)

Especially preferred radicals of the formula Gaba-(Ar) are derived from the following butyric acids: 4-amino-3-phenyl-, 4-amino-3-cyclohexyl-, 4-amino-3-(2-naphthyl)- and especially 4-amino-3-(1-naphthyl)-butyric acid.

As a result of the substitution with the radical Ar a centre of asymmetry is produced at the corresponding carbon atom of the acid chain which results in the presence of, in each case, two diastereoisomeric forms of the cyclopeptide according to the invention which may, if desired, be used separately or, alternatively, together, as a mixture of diastereoisomers, for the same purposes.

If, in the formula I, the symbol $Ac_4$ represents hydrogen, it denotes that the terminal amino group of the Lys residue is free. If this symbol represents the acyl radical Ac of a carboxylic acid, it denotes either the radical of an optionally substituted alkanecarboxylic acid, designated $Ac^1$, or the radical of a carboxylic acid that can be used as an amino-protecting group, designated $Ac^2$. The two radicals differ from each other fundamentally in that a radical $Ac^1$ cannot be detached from the $\epsilon$-amino group without at the same time impairing the peptidic amide bonds, whereas an acyl radical $Ac^2$ can be split off selectively with the amino group being liberated whilst the peptide structure is left undamaged.

The alkanecarboxylic acid forming the basis of the acyl radical $Ac^1$ has preferably not more than 18 carbon atoms if it is substituted and preferably not more than 8 carbon atoms if it is unsubstituted. The substituents are, on the one hand, hydroxyl, mercapto, lower alkylthio, such as methylthio, guanidino, carboxyl, carboxamido and especially primary amino groups, and, on the other hand, mono- or bicyclic hydrocarbyl or heterocyclyl radicals, such as especially phenyl, p-hydroxyphenyl, 1- or 2-naphthyl, 2-, 3- or 4-pyridyl, 2- or 3-indolyl, 2- or 4-imidazolyl, 2-, 4- or 5-thiazolyl, 2-thienyl or 2-furyl. The acid may carry one or more substituents of the same kind or different kinds, the total number of carbon atoms, including the carbon-containing substituents, being preferably not more than 18. Especially preferred are acyl radicals that are derived from singly branched or especially straight-chained unsubstituted alkane-(mono or di)-carboxylic acids, the former having a maximum of 18, and the latter a maximum of 9, carbon atoms, such as those derived from acetic, propionic, butyric, isobutyric, valeric, isovaleric, caproic, oenanthic, undecanoic, lauric, myristic, palmitic and stearic acid on the one hand, and malonic, succinic, glutaric, adipic, pimelic and suberic acid on the other hand.

Especially preferred are also acyl radicals that are derived from $\alpha$-amino acids of the L-series which are naturally occurring, especially as peptide-building blocks, and their closely related analogues, such as, especially, the "unnatural" enantiomers of the D-series. Of the preferred $\alpha$-amino acids, for example the following are most especially suitable: glycine, alanine, valine, leucine, isoleucine, phenylalanine, aspartic acid, glutamic acid, arginine, lysine and histidine, also $\beta$-alanine, $\alpha$-aminobutyric acid, $\gamma$-aminobutyric acid, norvaline, isovaline, norleucine and ornithine, and also asparagine, glutamine, tyrosine, tryptophan, methionine, threonine, serine, proline and hydroxyproline.

The carboxylic acid acyl radicals denoted by the symbol $Ac^2$ which can be used as amino-protecting groups are, for example, formyl, trifluoroacetyl or phthaloyl, or especially radicals that are derived from carbonic acid and, in particular, from monoesters thereof. These include acyl radicals that can be split off by acidolysis, such as especially the radicals of the type tert.-butoxycarbonyl, such as tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl, and also certain aralkoxycarbonyl radicals of the 2-(p-biphenylyl)-2-propoxycarbonyl type which are described in Swiss Pat. No. 509 266.

The acyl radical $Ac^2$ also includes acyl radicals that can be used as amino-protecting groups and can be split off by reduction or by means of bases, for example especially those of the benzyloxycarbonyl type, such as benzyloxycarbonyl itself and derivatives thereof which are substituted in the aromatic moiety by halogen atoms, nitro groups, lower alkoxy groups and/or lower alkyl radicals, such as p-chloro- and p-bromobenzyloxycarbonyl, p-nitrobenzyloxycarbonyl, p-methoxybenzyloxycarbonyl, p-tolyloxycarbonyl, and especially isonicotinyloxycarbonyl.

An acyl radical $Ac^2$ that is especially advantageous as an $\epsilon$-amino-protecting group is an ethoxycarbonyl radical that carries in the $\beta$-position a silyl group substituted by three hydrocarbon radicals, such as a triphenylsilyl, dimethyl-butyl-silyl or especially a trimethylsilyl group. A $\beta$-(trihydrocarbylsilyl)-ethoxycarbonyl radical of this type, such as $\beta$-(tri-lower alkylsilyl)-ethoxycarbonyl, for example especially $\beta$-(trimethysilyl)-ethoxycarbonyl, forms, together with the 2-amino group that is to be protected, a corresponding $\beta$-trihydrocarbylsilylethoxycarbonylamino group (for example the $\beta$-trimethylsilylethoxycarbonylamino group).

Especially preferred cyclic octapeptides of the formula I according to the invention are the following:

[D-Trp[8], Phe[12], Gaba[13]]-cyclosomatostatin(6-13)-octapeptide of the formula

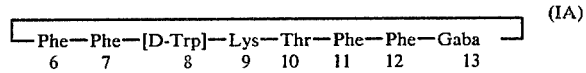

(IA)

| └─Phe—Phe—[D-Trp]—Lys—Thr—Phe—Phe—Gaba─┘ |
|  6    7      8      9    10   11   12   13  |

[D-Trp[8], D-Phe[12], Gaba[13]]-cyclosomatostatin(6-13)-octapeptide of the formula

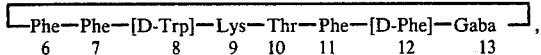

(IB)

and [D-(5F)-Thr⁸, Phe¹², Gaba¹³]-cyclosomatostatin(6-13)-octapeptide of the formula

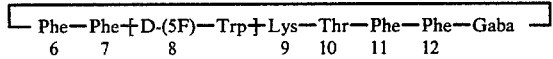

(IC)

and corresponding [Cha¹²]-analogues, i.e. those in which the phenyl ring of Phe¹² radical is saturated, and [Phg¹²]-analogues.

Those cyclopeptides characterised above by the formula I which contain a free carboxyl group in the radical $Ac_o$ may alternatively be in the form of salts, for example sodium, potassium, calcium or magnesium salts, or alternatively in the form of ammonium salts derived from ammonia or a physiologically tolerable organic nitrogen-containing base. Those cyclopeptides of the formula I, which are characterized above either in general terms or as being preferred, that contain a free amino group may alternatively be in the form of salts, that is acid addition salts. Suitable acid addition salts are especially physiologically tolerable salts with conventional therapeutically acceptable acids; of the inorganic acids, mention should be made of hydrohalic acids (such as hydrochloric acid), and also of sulphuric acid and phosphoric or pyrophosphoric acid; of the organic acids, mention should be made especially of sulphonic acids (such as benzenesulphonic acid or p-toluenesulphonic acid, or lower alkanesulphonic acids, such as methanesulphonic acid), also of carboxylic acids, such as acetic acid, lactic acid, palmitic and stearic acid, malic acid, tartaric acid, ascorbic acid and citric acid.

The peptides of the formula I according to the invention may alternatively be in the form of complexes. Complexes should be understood as being compounds the structures of which have not yet been fully clarified and that are formed when certain inorganic or organic substances are added to peptides and that impart to these a prolonged action. Such substances are described, for example, for ACTH and other adrenocorticotropically active peptides. Those that should be mentioned are, for example, inorganic compounds that are derived from metals such as calcium, magnesium, aluminium, cobalt and especially zinc, especially sparingly soluble salts, such as phosphates, pyrophosphates and polyphosphates, as well as hydroxides of these metals, also alkali metal polyphosphates, for example Calgon®N, Calgon®322, Calgon®188 or Polyron®12. Organic substances that prolong action are, for example, non-antigenic types of gelatin, for example polyoxygelatin, polyvinylpyrrolidone and carboxymethylcellulose, also sulphonic or phosphoric acid esters of alginic acid, dextran, polyphenols and polyalcohols, especially polyphloretin phosphate and phytic acid, and also polymers and copolymers of basic or, especially, acidic, amino acids, for example protamine or polyglutamic acid.

Unless otherwise indicated, the short forms of the amino acid residues refer to residues of the α-amino acids of the L-series that occur naturally.

Unless otherwise indicated, the term "lower" wherever it occurs in connection with an organic radical or a compound, indicates such a radical or compound having a maximum of 7 carbon atoms and preferably a maximum of 4 carbon atoms.

The novel cyclopeptides according to the invention have a physiological action that is fundamentally similar to the action of somatostatin. They can therefore be used advantageously in therapeutic indications similar to those of somatostatin, for example especially for the treatment of functional disorders in which the secretion of the somatotrophic hormone or glucagon is abnormally high, such as in the case of acromegaly or diabetes. Since they also inhibit blood losses in the gastrointestinal tract they can also be used successfully in this area of indication.

The cyclopeptides according to the invention are obtained by using conventional manufacturing processes of peptide chemistry which are known per se.

Thus, they are manufactured, for example by cyclising a linear peptide corresponding to the cyclopeptide, i.e. one which has the same amino acids in a sequence identical to that of the cyclic peptide according to the invention, an amide bond between any two adjacent ring-forming amino acids being, however, interrupted and replaced by corresponding terminal functional groups, i.e. a carboxyl group and an amino group, which may also be present in an activated form.

The compounds according to the invention are manufactured by cyclisation especially by cyclising a corresponding linear peptide of the formula $$H\text{—}[I_a]\text{—}V \hspace{2cm} (II)$$

in which $I_a$ represents a radical corresponding to the formula I in which the amide bond between any two adjacent amino acid residues of the peptide ring is interrupted, and V represents a free hydroxyl group, a hydroxyl group modified by an activating group or represents the hydrazino group —NH—NH₂, any amino, carboxyl and hydroxyl groups present that do not participate in the cyclisation reaction being, as required, in protected form and liberated subsequently, and, if desired, by acylating at a free amino group.

Of the linear peptides of the formula II, those in which the radical A or especially the radical B is present as a terminal amino acid in the radical [$I_a$] are preferred. These preferred starting materials are characterised by the formulae $$H\text{-B-Phe-Phe-trp-Lys}(Ac_x)\text{-Thr-Phe-A-V} \hspace{1cm} (IIa)$$

and especially $$H\text{-Phe-Phe-trp-Lys}(Ac_x)\text{-Thr-Phe-A-B-V} \hspace{1cm} (IIb)$$

in which $Ac_x$ represents the above-characterised acyl radical $Ac^1$ or an ε-amino-protecting group X, trp, A and B have the meanings mentioned at the beginning and V has the meanings given immediately above. Most especially preferred are compounds of the formulae IIa and IIb in which no cyclic hydrocarbyl radicals are present in the radical B.

A functional group represented by the symbol V supplements the carbonyl group of the C-terminal amino acid residue and forms together with that group a free carboxyl group, an activated ester group or the carbazolyl group, as the case may be.

The activating group by which the hydroxyl group is modified is especially one that forms the activated ester of N-hydroxysuccinimide, 1-hydroxybenzotriazole, N,N'-dicyclohexylisourea, 2,4,5-trichlorophenol, 2-nitrophenol, 4-nitrophenol, pentachlorophenol or pentafluorophenol but may also be a different activating group of this type known from peptide chemistry, cf. Houben-Weyl, volume 15/II.

The cyclisation according to the invention of the linear peptides of the formula II is carried out in a manner known per se by means of conventional coupling methods customarily used for the formation of the amide bond, the peptide starting materials, however, being used in a very low concentration in order to influence the course of the coupling operation in favour of intramolecular cyclisation at the expense of intermolecular polycondensation.

The linear peptides are advantageously used in an approximately $1.10^{-4}$ molar to approximately $1.10^{-2}$ molar concentration, preferably an approximately $1.10^{-3}$ molar concentration which corresponds to a weight/volume concentration of approximately 0.01 to 1.0%, preferably 0.1%. The reaction mixture can be correspondingly diluted from the start or this dilution can be produced continuously by the slow dropwise addition of the starting material, and optionally the other reagents, to the reaction mixture.

Cyclisation is preferably carried out, at a starting concentration indicated above, by (a) treating a starting material of the formula II, in which V represents a free hydroxyl group, while temporarily protecting other amino, carboxyl and hydroxyl groups present, with a carbodiimide, optionally in the presence of an active esterforming component, or (b) reacting with an organic base a starting material of the formula II, in which V represents a hydroxyl group modified to form the activated ester and the terminal amino group is present in protonated form, at least the amino group and carboxyl groups not participating in the cyclisation reaction being protected, or (c) first treating a starting material of the formula II, in which V represents the group —NHNH$_2$ and at least the amino group not participating in the cyclisation reaction is protected, with nitrous acid or a lower alkyl ester thereof under acidic conditions and then cyclising with excess organic base at an above-mentioned low concentration.

A carboxyl group is protected by a protecting group W in the manner described hereinbelow. For the protection of the amino and hydroxyl groups, the groups X and Y respectively, as defined hereinbelow, are advantageously used.

The cyclisation is carried out in suitable solvents, for example dioxan, tetrahydrofuran, acetonitrile, pyridine, dimethylformamide, dimethylacetamide, dimethyl sulphoxide, N-methylpyrrolidone, hexamethylphosphoric acid triamide, chloroform, methylene chloride or ethyl acetate, and mixtures thereof.

In process variant (a) the cyclisation is brought about by a carbodiimide, preferably N,N'-dicyclohexyl carbodiimide, which is advantageously used in excess; it is to be assumed that the starting material of the formula II having a free carboxyl group is first converted into an activated ester of dicyclohexylisourea (or an analogous isourea) and this active ester formed in situ immediately reacts further. The intermediate formation of an active ester can doubtless be attributed to the addition of an active ester-forming component as an auxiliary reagent; for this purpose, active ester-forming components customary in peptide chemistry may be used, such as, especially, 2,4,5-trichlorophenol, 2- or 4-nitrophenol, pentachlorophenol and pentafluorophenol, but, more especially, N-hydroxy compounds, among which N-hydroxysuccinimide, N-hydroxypiperidine and above all 1-hydroxybenzotriazole are especially advantageous. In the case of this variant, the operating temperature is generally 0°–70°, preferably 35°–55°.

In the case of variant (b) which is carried out with ready-prepared active esters, especially those already pointed out, cyclisation takes place spontaneously as soon as the terminal amino group is deprotonated by the organic base. The bases used are preferably quaternary or especially tertiary amines, for example triethylamine or N-ethylmorpholine. The operation is preferably carried out at 10°–30°, especially at room temperature.

In the case of variant (c), the first phase, i.e. the formation of the acid azide by treating with nitrous acid or an ester thereof, may advantageously be carried out at a considerably higher concentration of the starting materials than in the case of the subsequent cyclisation. The operation is advantageously carried out with approximately one equivalent of a lower alkyl nitrite, such as ethyl nitrite, isoamyl nitrite and especially tert.-butyl nitrite, in a hydrochloric acid medium at temperatures of from approximately −30° to approximately −5°, preferably approximately −20°; a slight excess of nitrite is permissible. The solution of the azide formed is then, after the necessary dilution, rendered basic at a temperature of from approximately 0° to approximately 35° by means of excess organic base, for example one of those mentioned above, and thereby made to cyclise spontaneously as in the case of process variant (b).

The narrower choice of protecting groups is determined by the specific purpose, it being necessary in the case where several functional groups are to be protected to select advantageous combinations.

As ε-amino-protecting groups X it is possible to use any of the amino-protecting groups that are customary in peptide chemistry, as are described synoptically in the appropriate reference works, for example in Houben-Weyl: Methoden der organischen Chemie; 4th edition, vol. 15/I, E. Wünsch (editor): Synthese von Peptiden; (Georg Thieme Verlag, Stuttgart; 1974).

Thus, for example, amino-protecting groups that can be split off by reduction or by bases can be used, for example carboxylic acid acyl radicals, such as formyl, trifluoroacetyl or phthaloyl, especially those of the benzyloxycarbonyl type, as are described above under the definition of the acyl radical Ac$^2$, or alternatively acyl groups derived from organic sulphonic acids (such as p-toluenesulphonyl), also benzenesulphenyl, o-nitrobenzenesulphenyl, and formyl, trifluoroacetyl or phthaloyl.

An advantageous ε-amino-protecting group X is also the β-(trihydrocarbylsilyl)-ethoxycarbonyl radical, as already described in detail under the meanings of Ac$^2$. Although this radical is stable under the conditions of acid hydrolysis and hydrogenolysis, it can be split off by the action of fluoride ions under quite specific, very mild conditions. In this respect, it behaves analogously to the β-silylethyl ester group described hereinbelow as a carboxyl-protecting group. (This similarity must be given particular consideration during the synthesis: except for isolated cases, the use of one of these protecting groups excludes the simultaneous use of the other protecting group.) Further details are given below in connection with the protection of the carboxyl group as β-silylethyl esters.

Groups that can be split off by acidolysis are most especially preferred as X, for example groups of the aralkyl type, such as benzhydryl and triphenylmethyl (trityl), or certain acyl radicals derived from carboxylic acids, especially aralkoxycarbonyl radicals of the 2-(p-biphenylyl)-2-propoxycarbonyl type, and more especially those of the tert.-butoxycarbonyl type, as already described in detail above under the meanings of the acyl radical $Ac^2$.

As the hydroxyl-protecting group Y there can be used any of the groups customarily used for this purpose in peptide chemistry, cf. the work cited above (Houben-Weyl). Groups that can be split off by acidolysis, such as 2-tetrahydropyranyl and more especially tert.-butyl, or tert.-butoxycarbonyl, are preferred. Alternatively, however, hydroxyl-protecting groups that can be split off by reduction or by means of bases can be used, for example benzyl and benzyloxycarbonyl groups that may be substituted in the aromatic moiety by halogen, nitro and/or lower alkoxy, or lower alkanoyl radicals, such as acetyl, or aroyl radicals, such as benzoyl. It is also possible to proceed without protecting hydroxyl groups if certain limiting measures are observed.

As carboxyl-protecting groups W there can be used any conventional group customarily used for this purpose, cf. the work cited above (Houben-Weyl). Thus, carboxyl groups are protected, for example by the formation of hydrazides or by esterification. Suitable for esterification are, for example, lower optionally substituted alkanols, such as methanol, ethanol, cyanomethyl alcohol, 2,2,2-trichloroethanol, benzoylmethyl alcohol or especially tert.-butyl alcohol, or alternatively an optionally substituted benzyl alcohol. An especially advantageous category of substituted alkanols is ethyl alcohols that contain in the β-position a tri-substituted silyl group, such as a triphenylsilyl, a dimethyl-butyl-silyl or especially a trimethylsilyl group. As described, for example, in Belgian Pat. No. 851,576, these alcohols are especially suitable for protecting carboxyl groups because, although the corresponding β-silylethyl esters, for example β-(trimethylsilyl)-ethyl ester, have the stability of conventional alkyl esters, they can be split off selectively under mild conditions by the action of fluoride ions while all the other protecting groups are retained.

The protecting groups X, Y and W, and also the α-amino-protecting group X' characterised in more detail below, are preferably so chosen that they can be split off under similar conditions; especially preferred in this connection are the groups already pointed out above that can be split off by acidolysis. All these protecting groups can thus be split off advantageously in a single operation; it is also possible, however, to use different kinds of protecting group and to split off each one individually.

If, however, an acyl radical $Ac^2$ in the $Lys^9$ residue, which was used to protect the ε-amino group during cyclisation, is to be retained in the end product of the formula I, the radicals X', Y and W should be so chosen that they can be split off while the radical $Ac^2$ is retained.

The protecting groups are split off in the generally known manner; acid hydrolysis (acidolysis) is carried out, for example, by means of trifluoroacetic acid, hydrochloric acid or hydrofluoric acid, or, in the case of protecting groups that are sensitive to acids, by means of a lower aliphatic carboxylic acid, such as formic acid and/or acetic acid, in the presence of water and optionally a poly-halogenated lower alkanol or lower alkanone, such as 1,1,1,3,3,3-hexafluoropropan-2-ol or hexafluoroacetone. The groups that can be split off by reduction, especially those which contain benzyl radicals, are preferably removed by hydrogenolysis, for example by hydrogenation under palladium catalysis. The isonicotinyloxycarbonyl group is split off preferably by zinc reduction.

The subsequent acylation of a corresponding peptide having a free ε-amino group in the lysine residue which is to be carried out if desired can be carried out optionally while temporarily protecting any free hydroxyl group present. The acylation is effected especially by treating an end product of the formula

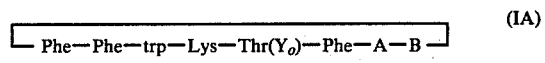
(IA)

in which A, B and trp have the meanings given at the beginning and $Y_o$ represents hydrogen or a hydroxyl-protecting group Y having the meaning defined in detail above, with an alkanecarboxylic acid $Ac_oOH$, in which $Ac_o$ represents a radical corresponding to the acyl radical Ac defined at the beginning, in which any amino and hydroxyl groups present may carry protecting groups X and X', and Y respectively, or with a reactive derivative of such an acid, and, if desired or necessary, liberating the amino and hydroxyl groups in the resulting product by splitting off the protecting groups X and X', and Y respectively.

The meaning of the symbol X' corresponds fairly extensively to that of the α-amino-protecting groups that are used in the synthesis of the peptide chain and described in detail hereinbelow. Preferably similar protecting groups are used both in the radical $Y_o$ and in the radical $Ac_o$ and are split off simultaneously following the acylation reaction.

A reactive derivative of an acid $Ac_oOH$ is, for example, an anhydride, especially a symmetric anhydride of the formula $Ac_o$—O—$Ac_o$ or a cyclic anhydride of a dicarboxylic acid, such as succinyl anhydride or glutaryl anhydride, or alternatively a mixed anhydride with a different organic acid, for example with trifluoroacetic acid, or especially with an inorganic acid, for example an acid azide or acid halide, especially an acid chloride. A reactive acid derivative is preferably an activated ester, for example one in which the acid $Ac_oOH$ is esterified with 2,4,5-trichlorophenol, pentachlorophenol, pentafluorophenol, 2-nitrophenol or especially 4-nitrophenol, or with an N-hydroxy compound, such as N-hydroxysuccinimide, 1-hydroxybenzotriazole or N-hydroxypiperidine, or alternatively with an N,N'-disubstituted isourea, such as especially N,N'-dicyclohexylisourea, or a similar activating component known from peptide chemistry, cf. Houben-Weyl: Methoden der organischen Chemie; 4th edition, vol. 15/I and II, E. Wünsch (editor): Synthese von Peptiden (Georg Thieme Verlag, Stuttgart; 1974).

The acylation is effected in a manner known per se, preferably in customary solvents, for example dioxan, tetrahydrofuran, acetonitrile, pyridine, dimethylformamide, dimethylacetamide, dimethyl sulphoxide, N-methylpyrrolidone, hexamethylphosphoric acid triamide, chloroform and methylene chloride, and in advantageous mixtures thereof. Alternatively, an organic base, for example a quaternary or especially a tertiary amine, such as triethylamine, N-ethylmorpholine or N-methylpiperidine, can be added to obtain the amin group which is to be acylated in deprotonated form. The reaction temperature is usually from −20° to +70° C., preferably from approximately 0° C. to room temperature.

Active esters are generally especially advantageous as acylating agents because they preferentially acylate amino groups before hydroxyl groups and thus render protection of hydroxyl groups virtually superfluous. In the case of dicarboxylic acids, however, cyclic anhydrides are preferred, if they are available. In order to avoid undesired O-acylation, only one equivalent of the acylating agent is usually used.

If, however, it is more advantageous for some reason to dispense with selective acylation, as may be the case especially in the reaction with acid chlorides, the acylating agent is used in excess and the co-acylated hydroxyl groups are liberated subsequently in the same conventional manner as the protected hydroxyl groups, especially by basic hydrolysis, for example with sodium or potassium hydroxide in the presence of water.

Those end products according to the invention which contain basic groups are obtained as bases or as acid addition salts depending on the method of isolation; these can subsequently be inter-converted in a manner known per se. Similarly, end products having acidic groups may also be in the form of salts, it being possible to convert each form into the other in known manner.

The formation of the above-mentioned complexes also is carried out according to known methods; complexes with sparingly soluble metal compounds, for example aluminium or zinc compounds, are produced preferably in a manner analogous to that known for ACTH, for example by reaction with a soluble salt of the metal concerned, for example zinc chloride or zinc sulphate, and precipitation with an alkali metal phosphate and/or hydroxide. Complexes with organic compounds, such as polyoxygelatine, carboxymethylcellulose, polyvinylpyrrolidone, polyphloretin phosphate, polyglutamic acid, etc. are obtained by mixing these substances with the peptide in aqueous solution. In the same manner, insoluble compounds may also be manufactured with alkali metal polyphosphates.

The starting materials of the above-characterised formula II and, unless stated otherwise, the intermediates used for the synthesis thereof, are new and, in some cases, can be used advantageously also for the synthesis of other somatostatin analogues, for example those having analogous amino acid partial sequences. The invention relates to these starting materials and the processes for the manufacture thereof. They are obtained by methods known per se, by condensing with one another, in any time sequence, the amino acids and smaller peptide units necessary for their synthesis, with the formation of CO—NH bonds, it being possible to protect temporarily any functional groups not participating in the reaction.

In the manufacture of these starting materials, and also of all the necessary intermediates, suitable protecting groups for the terminal α-amino and carboxyl groups are especially the protecting groups that are customarily used in the synthesis of long-chain peptides and that can be split off readily and selectively, for example by solvolysis or reduction. They have already been mentioned above several times under the symbols X' and W, respectively.

Examples of α-amino-protecting groups X' are: di- or triaryl-lower alkyl groups optionally substituted, for example, by halogen, nitro, lower alkyl or lower alkoxy, such as diphenylmethyl or triphenylmethyl groups, for example benzhydryl, trityl, di-(p-methoxy)-benzhydryl, or especially groups derived from carbonic acid that can be split off by hydrogenolysis, such as benzyloxycarbonyl groups optionally substituted in the aromatic moiety by halogen atoms, nitro groups, lower alkyl or lower alkoxy groups, for example benzyloxycarbonyl, p-bromo- or p-chlorobenzyloxycarbonyl, p-nitrobenzyloxycarbonyl, p-methoxybenzyloxycarbonyl; also 2-(p-biphenylyl)-2-propoxycarbonyl and similar aryloxycarbonyl groups described in Swiss Pat. No. 509,266. It must be ensured that the α-amino-protecting group X' can be split off selectively while the optionally present ε-amino-protecting group X of the lysine residue in the 9 position is retained. Furthermore, it is often advantageous if, during the splitting off of the α-amino-protecting group, an optionally present carboxyl- or hydroxyl-protecting group W or Y also remains undamaged.

The carboxyl-protecting groups for this purpose are the same as those discussed above in connection with the corresponding meaning of the symbol W.

These protecting groups can be split off in known manner. Thus, the benzyloxycarbonyl group can be split off by hydrogenolysis, the N-trityl group by mineral acids, such as hydrohalic acids, for example hydrofluoric acid or preferably hydrochloric acid, or an organic acid, such as formic acid, acetic acid, chloroacetic acid or trifluoroacetic acid, in aqueous or absolute trifluoroethanol as the solvent (cf. German Offenlegungsschrift DT 2 346 147) or with aqueous acetic acid; the tert.-butoxycarbonyl group can be split off with trifluoroacetic acid or hydrochloric acid, the 2-(p-biphenylyl)-isopropoxycarbonyl group with aqueous acetic acid or, for example, a mixture of glacial acetic acid, formic acid (82.8% strength) and water (7:1:2) or in accordance with the process described in DT-OS 2 346 147.

The β-silylethyl ester groups are split off preferably with reagents that yield fluoride ions, for example fluorides of quaternary organic bases, such as tetraethylammonium fluoride. Alternatively, however, they may be split off, in the same manner as conventional alkyl esters, by alkaline hydrolysis, for example by means of alkali metal hydroxides, carbonates or bicarbonates, or may be converted into the corresponding carbazoyl groups by hydrazinolysis, for example by means of hydrazine hydrate. Acidolysis is preferably used for splitting off tert.-butyl esters and hydrogenolysis for benzyl esters.

The condensation of the amino acids and/or peptide units which must be effected for the manufacture of the starting materials of the formula II is carried out in a manner known per se, preferably by linking an amino acid or a peptide having a protected α-amino group and an optionally activated terminal carboxyl group (=active component) to an amino acid or a peptide having a free α-amino group and a free or protected, for example esterified, terminal carboxyl group (=passive component), liberating the terminal amino group in the product so formed and reacting this peptide, which contains a free α-amino group and an optionally protected terminal carboxyl group, with a further active component, i.e. an amino acid or a peptide having an activated terminal carboxyl group and a protected α-amino group, and so on. The carboxyl group can be activated, for example, by converting it into an acid azid, anhydride, imidazolide, isoxazolide or an activated ester, such as one of those mentioned hereinbelow, or by reacting it with a carbodiimide, such as N,N'-dicyclohexyl carbodiimide, optionally with the addition of N-hydroxysuccinimide or an unsubstituted or, for example, a halogen-, methyl- or methoxy-substituted 1-hydroxybenzotriazole or 4-hydroxybenzo-1,2,3-triazine-3-oxide (inter alia cf. DT No. 1 917 690, DT No. 1,937 656, DT No. 2 202 613), or especially N-hydroxy-5-norbornene-2,3-dicarboximide, or with N,N'-carbonyldiimidazole. The most usual coupling method is the carbodiimide method, also the azide method, the activated esters method and the anhydride method, the Merrifield method and the method using N-carboxyanhydrides or N-thiocarboxyanhydrides.

Suitable for the formation of activated esters, such as those mentioned above, are, for example, phenols and thiophenols optionally substituted by electron-attracting substituents, such as phenol, thiophenol, thiocresol, p-nitrothiophenol, 2,4,5- and 2,4,6-trichlorophenol, pentachlorophenol, o- and p-nitrophenol, 2,4-dinitrophenol, and p-cyanophenol, and also, for example, N-hydroxysuccinimide, N-hydroxyphthalimide and N-hydroxypiperidine.

In an especially preferred method of manufacture of the peptides of the formula II, the coupling method used is the carbodiimide method with N,N'-dicyclohexyl carbodiimide in the presence of 1-hydroxybenzotriazole. The terminal carboxyl group is protected in the form of the β-(trimethylsilyl)-ethyl ester, and the α-amino group of the active component is protected by the benzyloxycarbonyl group which is split off by hydrogenolysis after each coupling step. In order to protect the ε-amino group of the lysine residue in the 9-position, acylation with the tert.-butoxycarbonyl group is used and, for the hydroxyl group of the threonine residues, etherification with the tert.-butyl group. These two protecting groups may, if desired, be split off finally in one step by acid hydrolysis, for example by means of trifluoroacetic acid, hydrochloric acid or hydrofluoric acid. If the ε-amino group of the lysine residue in the 9-position is acylated by Ac¹ from the start, it requires no protection.

Depending on the procedure used, the compounds of the formula II are obtained, depending on their character, in the form of bases or acid addition salts or, alternatively, in the form of acids or their salts. The bases can be obtained from the acid addition salts in a manner known per se. Therapeutically acceptable acid addition salts can, in their turn, be obtained from the bases by reacting with acids, for example with those that form the above-mentioned salts. Acids and their salts stand in a similar relationship to each other.

Owing to the close relationship between the new compounds in free form and in the form of their salts, hereinbefore and hereinafter the term "free compounds" shall, if desired, also include the salts thereof and the term "salts" shall, if desired, also include the free compounds, where appropriate according to meaning and purpose.

The invention relates also to those embodiments of the process in which a compound obtained as an intermediate at any stage of the process is used as starting material and the remaining process steps are carried out, or in which a starting material is formed under the reaction conditions or is used in the form of a derivative, optionally a salt.

Among such embodiments of the process according to the invention, there should be especially emphasised those in which the end products of the formula I defined at the beginning are manufactured as follows: in corresponding intermediates which can be obtained, for example, by cyclisation and in which at least some of the amino, hydroxyl and/or carboxyl groups present are in protected form, these groups are liberated. This embodiment, which results very generally in compounds of the formula

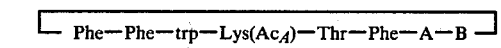   I in which trp represents L-Trp, D-Trp or an analogous radical which carries a halogen atom in the indole nucleus, $Ac_A$ represents a radical Ac of a carboxylic acid present at the ε-amino group or preferably represents hydrogen, A represents L-Phe, D-Phe, L-Phg or D-Phg or a corresponding radical having a substituted or saturated phenyl ring, and B represents the residue of a γ- or -amino-lower alkanecarboxylic acid which may carry at one of its carbon atoms an optionally substituted cyclic hydrocarbyl radical Ar, is characterised in that, in a cyclic compound of corresponding structure, in which at least one of the amino, hydroxyl and/or carboxyl groups present carries a protecting group X, Y and W respectively, the protecting group(s) is(are) split off and, if desired, one or more additional measures, such as acylation of the free amino group, salt formation or complex formation, is carried out.

An especially preferred method of carrying out this process is connected with the manufacture of end products of the formula I in which $Ac_A$ represents hydrogen, i.e. the manufacture of compounds of the formula

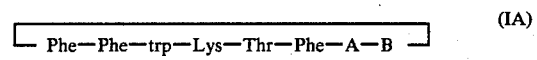   (IA)

in which trp, A and B have the general and preferred meanings given at the beginning, and is characterised in that in a corresponding peptide of the formula

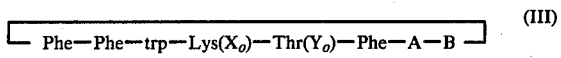   (III)

in which trp, A and B have the meanings given above, $X_o$ represents an ε-amino-protecting group X or hydrogen and $Y_o$ represents a hydroxyl-protecting group Y or hydrogen, it being possible for only one of the symbols $X_o$ and $Y_o$ to represent hydrogen, the protecting group(s) is(are) split off and, if desired, a resulting basic compound is converted into an acid addition salt, or a resulting acid addition salt is converted into the corresponding base and/or a resulting compound is converted into a complex thereof.

Preferred protecting groups X and Y have already been discussed above; in particular, combinations of X and Y which can be split off under the same conditions are chosen and preferably, for example, those radicals described above which can be split off by acidolysis (such as especially those of the tert.-butyl type.

In the process of the present invention, the starting materials used are preferably those that result in the compounds described at the beginning as especially valuable.

The present invention relates also to pharmaceutical preparations that contain compounds of the formula I or pharmaceutically acceptable salts or complexes thereof. These preparations may be used especially in the above-mentioned indications if they are administered intraperitoneally, such as intravenously, intramuscularly or subcutaneously, or also intranasally. The necessary dose depends on the particular disorder to be treated, its severity and the duration of therapy. The number and quantity of the individual doses and also the administration scheme can best be determined on the basis of an individual examination of the patient concerned. The method of determining these factors is known to the man skilled in the art. As a rule, however, in the case of injection, a therapeutically active quantity of a compound of this type lies in the dosage range of approximately 0.001 to approximately 0.2 mg/kg body weight. Preferably, the range is approximately 0.0015 to approximately 0.15 mg/kg body weight and administration is by intravenous infusion or subcutaneous injection. Accordingly, pharmaceutical preparations for parenteral administration in unit dose form contain per dose, depending on the type of medication, approximately 0.08 to approximately 15 mg of one of the compounds according to the invention. Apart from the active substance, they usually also contain a buffer, for example a phosphate buffer, that is to maintain the pH between approximately 3.5 and 7, and also sodium chloride, mannitol or sorbitol for adjusting the isotonicity. They may be in freeze-dried or dissolved form and solutions may advantageously contain an antibacterially active preservative, for example 0.2–0.3% of 4-hydroxybenzoic acid methyl ester or ethyl ester. If the active substance in such preparations is to be in the form of a complex having a prolonged duration of action then it must be formed directly by adding the complex-forming components to an injection solution that is prepared, for example, according to the abovementioned methods. A suitable additive is, for example, 0.1–1.0% by weight of a zinc(II) salt (for example sulphate) in conjunction with 0.5–5.0% by weight of protamine (for example as a sulphate), calculated on the total volume of the injection solution; this preparation is in the form of a solution having a pH of 3.5 to approximately 6.5 or in the form of a suspension having a pH of approximately 7.5 to 8.0.

A preparation for intranasal administration may be an aqueous solution or gel, an oily solution or suspension, or alternatively a fat-containing salve. A preparation in the form of an aqueous solution is obtained, for example, by dissolving the active substance of the formula I, or a therapeutically acceptable acid addition salt thereof, in an aqueous buffer solution having a pH of up to 7.2 and adding a substance producing isotonicity. A polymeric adhesive, for example polyvinylpyrrolidone, and/or a preservative are advantageously added to the aqueous solution. The individual dose is approximately 0.08 to approximately 15 mg, preferably 0.25 to 10 mg, which are contained in approximately 0.05 ml of a solution or 0.05 g of a gel.

An oily form of medication for intranasal administration is obtained, for example, by suspending a peptide of the formula I, or a therapeutically acceptable acid addition salt thereof, in an oil, optionally with the addition of swelling agents, such as aluminium stearate, and/or interfacially active agents (surfactants), the HLB value ("hydrophilic-lipophilic balance") of which is less than 10, such as fatty acid monoesters of polyhydric alcohols, for example glycerine monostearate, sorbitan monolaurate, sorbitan monostearate or sorbitan monooleate. A fat-containing salve is obtained, for example, by suspending the active substance according to the invention in a spreadable fat base, optionally with the addition of a surfactant having a HLB value of less than 10. An emulsion salve is obtained by triturating an aqueous solution of the peptide active substance in a soft, spreadable fat base with the addition of a surfactant the HLB value of which is less than 10. All these intranasal forms of medication may also contain preservatives. The individual doses are approximately 0.08 to approximately 15 mg, preferably 0.25 to 10 mg, contained in approximately 0.05 to approximately 0.1 g of the base substance.

Also suitable for intranasal administration are inhalation or insufflation preparations, such as insufflation capsules that permit the active substance to be insufflated in the form of a powder with respiratory air, or aerosols or sprays that can disperse the pharmacological active substance in the form of a powder or in the form of drops of a solution or suspension. Preparations having powder-dispersing properties generally contain adjuncts in addition to the active substance: insufflation capsules contain, for example, solid carriers, such as lactose; aerosol or spray preparations contain, for example, a liquid propellant having a boiling point of below room temperature and, if desired, other carriers, such as liquid or solid non-ionic or anionic surfactants and/or solid diluents. Preparations in which the pharmacological active substance is in solution contain, in addition to this, a suitable propellant and also, if necessary, an additional solvent and/or a stabiliser. Instead of the propellant, it is also possible to use compressed air which is produced when required by means of a suitable compressing and releasing device.

The invention relates also to the use of the novel compounds of the formula I and therapeutically acceptable salts and complexes thereof as pharmacologically active compounds, especially in indications mentioned at the beginning, preferably in the form of pharmaceutical preparations. The daily dose administered to a warm-blooded animal weighing approximately 70 kg is from approximately 0.1 to approximately 120 mg.

The invention is illustrated in the following Examples but is not limited by these. Temperatures are given in degrees Centigrade; the conventional short forms, for example those compiled in "Synthese von Peptiden" (editor: E. Wünsch), volume XV of "Methoden der org. Chemie" (Houben-Weyl) (1974; G. Thieme, Stuttgart) are used as abbreviations, for example for denoting amino acids, peptides, protecting groups, etc. The following abbreviations, in particular, are used:

| | |
|---|---|
| Boc | tert.—butoxycarbonyl |
| But | tert.—butyl (as ether-forming group) |
| OBzl | benzyloxy (as ester-forming group) |
| OTmse | 2-(trimethylsilyl)-ethoxy (as ester-forming group) |
| Z | benzyloxycarbonyl |
| and | |
| TLC | thin layer chromatography |
| DCCI | dicyclohexyl carbodiimide |
| DMF | dimethylformamide |

In TLC, unless otherwise indicated, silica gel is used as the adsorbent and the following systems are used as eluants (in proportions by volume)

System:
- 100: ethyl acetate/pyridine/glacial acetic acid/water (62:21:6:11)
- 157A: chloroform/methanol/glacial acetic acid/water (90:10:0.5:1)
- 157C: chloroform/methanol/glacial acetic acid/water (75:27:0.5:5)

EXAMPLE 1

[D-Trp$^8$,Phe$^{12}$,Gaba$^{13}$]-cyclosomatostatin(6-13)octapeptide

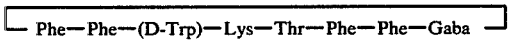

A solution of 212 mg of H-Phe-Phe-(D-Trp)-Lys(Boc)Thr(But)-Phe-Phe-Gaba-OH, 255 mg of 1-hydroxybenzotriazole monohydrate and 345 mg of DCCI in 150 ml of DMF is maintained at 50° for 18 hours. After the addition of 300 mg of oxalic acid the mixture is concentrated to a small volume in a high vacuum, the precipitated dicyclohexylurea is filtered off with suction and the product is precipitated by adding the filtrate dropwise to aqueous sodium bicarbonate. Purification is carried out by countercurrent distribution over 900 stages in the system methanol/water/chloroform/carbon tetrachloride (2000:500:660:1160 parts by volume). The fractions (K=0.3) that are pure according to TLC are combined, concentrated by evaporation in vacuo and lyophilised from tert.-butanol.

TLC: [system 157A]
$R_f$ 0.48.

While cooling with ice, 16 ml of 90% by volume trifluoroacetic acid containing 0.16 ml of mercaptoethanol are added to 160 mg of the resulting cyclopeptide of the formula

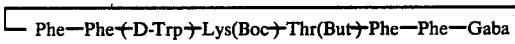

and the mixture is then left for 30 minutes at room temperature. After concentration in vacuo to approximately 2 ml, precipitation is effected with ether/hexane (1:2) and the resulting trifluoroacetate, dissolved in a mixture of 1% aqueous acetic acid and tert.-butanol (9:1), is filtered through 10 ml of Amberlite IR 45 ® (in the acetate form). The resulting eluate is concentrated by evaporation in vacuo, and the residue is subjected to countercurrent distribution over 900 stages in the system tert.-butanol/methanol/toluene/buffer (800:340:800:1140), the buffer containing 2.2 g of ammonium acetate and 1.63 ml of glacial acetic acid in 1 liter of water. The fractions (K=0.62) that are pure according to TLC are combined, concentrated in vacuo and lyophilised from aqueous tert.-butanol. The resulting title compound is uniform by TLC.

TLC: system 100: $R_f$ 0.29
157C: $R_f$ 0.28

The starting material is obtained as follows:

Stage 1.1

Boc-Phe-Gaba-OBzl 2.65 g of Boc-Phe-OH and 3.65 g of H-Gaba-OBzl-p-toluenesulphonate (cf. European Pat. No. 78 100 994.8, published as No. 0001 295, Example 1, Stage 1.7A) are suspended in 18 ml of acetonitrile and, while stirring at 5°, the suspension is treated in succession with 1.11 ml of N-methylmorpholine, 765 mg of 1-hydroxybenzotriazole monohydrate and 2.47 g of DCCI and stirred for a further 15 hours at 5°. The excess DCCI is destroyed with oxalic acid, the precipitated dicyclohexylurea is filtered off and the filtrate, having been diluted with 200 ml of ethyl acetate, is extracted by shaking with dilute hydrochloric acid and sodium bicarbonate solution. After drying over sodium sulphate, the organic phase is concentrated by evaporation in vacuo and the resulting product is used in Stage 1.2 without further purification.

TLC: [toluene/ethyl acetate (1:9)]
$R_f$ 0.54.

Stage 1.2

H-Phe-Gaba-OBzl-hydrochloride 12.8 ml of 1.2 N hydrochloric acid in 90% by volume trifluoroethanol are added to a solution of 2.25 g of Boc-Phe-Gaba-OBzl (Stage 1.1) in 2.2 ml of 90% by volume aqueous trifluoroethanol. After 30 minutes, 50 ml of tert.-butanol are added, the solution is concentrated in vacuo and the remaining solvent is removed by lyophilisation. The residue is recrystallised from ethyl acetate. M.P. 101°–102°

TLC: [chloroform/methanol (8:2)]
$R_f$ 0.49

Stage 1.3

Z-Phe-Phe-(D-Trp)-Lys(Boc)-Thr(But)-Phe-Phe-Gaba-OBzl 233 mg of Z-Phe-Phe-(D-Trp)-Lys(Boc)-Thr(But)-Phe-OH (cf. the European Patent Application mentioned above, Example 7.2), 94 mg of H-Phe-Gaba-OBzl-hydrochloride (Stage 1.2) and 46 mg of 1-hydroxybenzotriazole monohydrate are dissolved while warm in 0.5 ml of DMF. After cooling to −10°, 28 μl of N-methylmorpholine and a solution of 53 mg of DCCI in 0.1 ml of DMF are added, the mixture is stirred for a further hour and then left for 20 hours at −5°. The thick mass is triturated with ether, the undissolved material is filtered off with suction and washed with cold methanol. Apart from traces of dicyclohexylurea, the product is pure according to TLC.

TLC: [chloroform/methanol (95:5)]
$R_f$ 0.42

Stage 1.4

H-Phe-Phe-(D-Trp)-Lys(Boc)-Thr(But)-Phe-Phe-Gaba-OH

After the addition of 25 mg of palladium-on-carbon (10%) a solution of 250 mg of Z-Phe-Phe-(D-Trp)-Lys(Boc)-Thr(But)-Phe-Phe-Gaba-OBzl (Stage 1.3) in 15 ml of DMF is hydrogenated for 2 hours. After filtering off the catalyst the filtrate is concentrated to dryness by evaporation in a high vacuum and the residue is used for the cyclisation without further purification.

TLC: [system 157A]
$R_f$ 0.12

EXAMPLE 2

[D-Trp⁸,D-Phe¹²,Gaba¹³]-cyclosomatostatin(6-13)-octapeptide

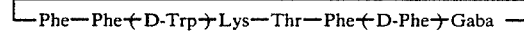

In a manner analogous to that described in Example 1, H-Phe-Phe-(D-Trp)-Lys(Boc)-Thr(But)-Phe-(D-Phe)-Gaba-OH is cyclised by means of DCCI and 1-hydroxybenzotriazole. The crude product is purified by countercurrent distribution. (K=0.3)

TLC: [system 157A]
$R_f$ 0.49

The resulting cyclic peptide of the formula

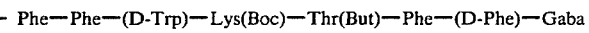

is treated with trifluoroacetic acid and purified by countercurrent distribution (K=0.67) analogously to Example 1.

| TLC: system 157C: | $R_f$ 0.32 |
|---|---|
| 100: | $R_f$ 0.32 |

The starting material is obtained as follows:

Stage 2.1

Boc-(D-Phe)-Gaba-OBzl

The compound is manufactured from Boc-(D-Phe)-OH and H-Gaba-OBzl-p-toluenesulphonate in a manner analogous to that described in Example 1, stage 1.1

TLC: [toluene/ethyl acetate (1:9)]
$R_f$ 0.54

Stage 2.2

H-(D-Phe)-Gaba-OBzl-hydrochloride

This compound is obtained in a manner analogous to that described in Example 1, Stage 1.2 by splitting off the Boc groups from Boc-(D-Phe)-Gaba-OBzl. M.p. 99°–100°

TLC: [chloroform/methanol (8:2)]
$R_f$ 0.49

Stage 2.3

Z-Phe-Phe-(D-Trp)-Lys(Boc)-Thr(But)-Phe-(D-Phe)-Gaba-OBzl

The compound is obtained in a manner analogous to that described in Example 1, Stage 1.3 by condensation of Z-Phe-Phe-(D-Trp)-Lys(Boc)-Thr(But)-Phe-OH and H-(D-Phe)-Gaba-OBzl-hydrochloride (Stage 2.2) with DCCI in the presence of 1-hydroxybenzotriazole and N-methylmorpholine.

TLC: [system 157A]
$R_f$ 0.68

Stage 2.4

H-Phe-Phe-(D-Trp)-Lys(Boc)-Thr(But)-Phe-(D-Phe)-Gaba-OH

This compound is obtained in a manner analogous to that described in Example 1, Stage 1.4 by hydrogenating Z-Phe-Phe-(D-Trp)-Lys(Boc)-Thr(But)-Phe-(D-Phe)-Gaba-OBzl (Stage 2.3) and is cyclised without purification.

We claim:

1. A cyclic octapeptide of the formula

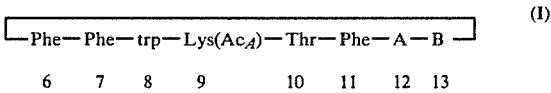

in which trp represent L-Trp, D-Trp or an analogous radical which carries a halogen atom in the indole nucleus, $Ac_A$ represents hydrogen, A represents L-Phe, D-Phe, L-Phg or D-Phg, or the analogus residues having the cyclohexyl or p-hydroxyphenyl radical substituted for the phenyl radical, and B represents Gaba which is the residue of the unsubstituted α-aminobutyric acid, or Gaba (Ar), which is an analogus residue carrying in the β-position a mono- or bicyclic aryl radical Ar having not more than 12 carbon atoms, and also pharmacologically tolerable salts and activity-prolonging therapeutically acceptable complexes thereof.

2. A cyclic octapeptide according to claim 1, in which, formula I trp represents D-Trp or D-(5F)Trp, $AC_A$ represents hydrogen, A represents L-Phe, D-Phe, L-Phg or D-Phg, or the analogus residues having the cyclohexyl or p-hydroxyphenyl radical substituted for the phenyl radical, and B represents Gaba which is the residue of the unsubstituted α-aminobutyric acid, or Gaba (Ar), which is an analogus residue carrying in the β-position a mono- or bicyclic aryl radical Ar having not more than 12 carbon atoms, and also pharmacologically tolerable salts and activity-prolonging therapeutically acceptable complexes thereof.

3. A cyclic peptide, according to claim 1, in which, in the formula I, trp represents D-Trp or D-(5F)Trp, $Ac_A$ represents hydrogen, A represents L-Phe, D-Phe, L-Phg or D-Phg, or the analogus residues having the cyclohexyl or p-hydroxyphenyl radical substituted for the phenyl radical, and B represents the residue of the unsubstituted γ-aminobutyric acid, and also pharmacologically tolerable salts and activity prolonging therapeutically acceptable complexes thereof.

4. [D-Trp⁸,Phe¹²,Gaba¹³]-cyclosomatostatin(6-13)-octapeptide and pharmacologically activity prolonging therapeutically acceptable complexes thereof.

5. [D-Trp⁸,D-Phe¹²,Gaba¹³]-cyclosomatostatin(6-13)octapeptide and pharmacologically activity prolonging therapeutically acceptable complexes thereof.

6. A pharmaceutical preparation for the treatment of diabetes and/or gastrointestinal bleeding in humans and mammals, containing an effective amount of a compound according to any one of claims 1-5.

7. A therapeutic method for the treatment of diabetes and/or gastrointestinal bleeding in humans and mammals by administration of a therapeutically effective dose of a compound according to any one of claims 1-5 alone or in the form of a pharmaceutical preparation.

* * * * *